United States Patent [19]

Bowman et al.

[11] Patent Number: 5,714,639
[45] Date of Patent: Feb. 3, 1998

[54] DOUBLE METAL CYANIDE CATALYSTS AND METHODS FOR MAKING THEM

[75] Inventors: Paul T. Bowman, Hurricane; Harry R. Hinney, Cross Lanes; Robert L. Meeker, Charleston, all of W. Va.

[73] Assignee: Arco Chemical Technology, L.P., Greenville, Del.

[21] Appl. No.: 803,657

[22] Filed: Feb. 21, 1997

Related U.S. Application Data

[62] Division of Ser. No. 588,751, Jan. 19, 1996, Pat. No. 5,639,705.

[51] Int. Cl.$^6$ .................... B01J 27/26; C08L 63/00
[52] U.S. Cl. .................... 568/620; 568/607; 549/513
[58] Field of Search ................ 502/175, 200; 525/118; 549/513

[56] References Cited

U.S. PATENT DOCUMENTS

| | | |
|---|---|---|
| 3,278,457 | 10/1966 | Milgrom . |
| 3,278,458 | 10/1966 | Belner . |
| 3,538,043 | 11/1970 | Herold . |
| 3,829,505 | 8/1974 | Herold . |
| 3,900,518 | 8/1975 | Milgrom . |
| 3,941,849 | 3/1976 | Herold . |
| 4,472,560 | 9/1984 | Kayper et al. .................... 526/117 |
| 4,477,589 | 10/1984 | Vander Hulst et al. .................... 502/169 |
| 5,145,883 | 9/1992 | Saito et al. .................... 521/172 |
| 5,158,922 | 10/1992 | Hinney et al. .................... 502/175 |
| 5,223,583 | 6/1993 | Higuchi et al. .................... 525/404 |
| 5,470,813 | 11/1995 | Le-Khac .................... 502/175 |

FOREIGN PATENT DOCUMENTS 4145123  5/1992  Japan .

OTHER PUBLICATIONS

J.L. Schuchardt and S.D. Harper, SPI Proceedings, 32nd Annual Tech./Market Conf. (1989) 360 no month available.

*Primary Examiner*—C. Warren Ivy
*Assistant Examiner*—Lyman H. Smith
*Attorney, Agent, or Firm*—Jonathan L. Schuchardt

[57] ABSTRACT

Improved double metal cyanide (DMC) catalysts useful for making epoxide polymers are disclosed. One catalyst is a paste of a double metal cyanide (DMC) compound, an organic complexing agent, and water. The paste comprises at least about 90 wt. % of particles having a particle size within the range of about 0.1 to about 10 microns as measured by light scattering in polyether polyol dispersions of the catalyst particles. Preferred catalysts have a bimodal particle size distribution. The paste catalyst is more active and simpler to prepare than powder DMC catalysts. Polyols made from the paste catalyst have low unsaturations, low viscosities, and narrow molecular weight distributions, and are useful in making a variety of polyurethane products.

11 Claims, No Drawings

DOUBLE METAL CYANIDE CATALYSTS AND METHODS FOR MAKING THEM

This is a division of application Ser. No. 08/588,751, Filed Jan. 19, 1996 now U.S. Pat. No. 5,639,705.

FIELD OF THE INVENTION

The invention relates to improved double metal cyanide (DMC) catalysts and methods for making them. The catalysts are highly active in epoxide polymerization reactions used to prepare polyether polyols. Polyether polyols are valuable polymer intermediates for making polyurethane foams, elastomers, sealants, coatings, and adhesives.

BACKGROUND OF THE INVENTION

Double metal cyanide (DMC) complex compounds are well known catalysts for epoxide polymerization. The catalysts are highly active, and give polyether polyols that have low unsaturation compared with similar polyols made using basic (e.g., KOH) catalysts. Polyols with low unsaturation are desirable because they give polyurethanes with an excellent balance of physical and mechanical properties.

DMC catalysts are made by reacting aqueous solutions of metal salts and metal cyanide salts to form a precipitate of the DMC compound. A low molecular weight organic complexing agent, typically an ether or an alcohol, is included in the preparation. The complexing agent is incorporated into the catalyst structure, and is required for an active catalyst. In a typical catalyst preparation, the precipitated DMC compound is washed several times with aqueous solutions containing the organic complexing agent, and is isolated by centrifugation or filtration. Finally, the catalyst is dried to a solid cake, usually in a vacuum oven. The dried catalyst is then crushed to give a free-flowing powder. The powder form of catalyst is commonly used for polymerizing epoxides. U.S. Pat. No. 3,829,505 and Jap. Pat. Appl. Kokai No. 4-145123 illustrate typical catalyst preparations; each includes details of how to dry and crush the catalyst before use.

Van der Hulst et al. (U.S. Pat. No. 4,477,589) teaches the preparation of powder DMC catalysts. In addition, this reference teaches that suspensions of DMC catalysts in propoxylated glycerin starter polyols can be used, thereby eliminating the need to isolate a powder catalyst. In making a suspension, a DMC catalyst is precipitated in the usual way. The aqueous catalyst mixture is treated with an organic complexing agent, and the suspension of catalyst, water, and complexing agent is combined with propoxylated glycerin. This mixture is stripped to remove water and excess organic complexing agent, leaving a suspension of DMC catalyst in propoxylated glycerin. The suspension, which contains about 3 to 5 wt. % of DMC catalyst, is then used as a catalyst in the reaction of additional starter polyol and propylene oxide to make a polyol. Thus, the reference teaches to use as a catalyst either a powder DMC catalyst or a dilute suspension of DMC compound in propoxylated glycerin. Despite the apparent advantages of the suspension approach, powder catalysts have been more widely used.

Powder DMC catalysts having exceptional activity for epoxide polymerization are now known in the art. See, for example, U.S. Pat. No. 5,470,813. However, even the best powder DMC catalysts have some disadvantages. First, drying the catalyst after isolation is time-consuming and requires a vacuum oven. Drying large quantities of catalyst is especially taxing. Second, the dried catalyst must be crushed to produce a powder. This step requires an expensive crusher, pulverizer, or mill. Both steps are costly in terms of capital costs, labor, and time requirements, and they add significantly to the overall cost of production.

The drying and crushing steps can adversely affect catalyst quality and performance. Excessive heating during the drying stage can cause catalyst degradation and reduced activity. Catalyst heat-up due to friction during crushing of the catalyst can also adversely impact catalyst performance. Variations in how crushing and drying are done from batch to batch can result in inconsistent catalyst performance and variations in polyol quality.

Improved double metal cyanide catalysts are needed. Preferred catalysts will have high activity, as those described in U.S. Pat. No. 5,470,813. Particularly needed are catalysts that can be made without drying or crushing steps, which add significantly to the overall cost of production. An especially valuable catalyst could be made with improved batch-to-batch consistency, and would enhance the quality of polyether polyols made using the catalyst.

SUMMARY OF THE INVENTION

The invention is an improved double metal cyanide (DMC) catalyst. The catalyst comprises a paste of a DMC compound, an organic complexing agent, and water. The paste comprises at least about 90 wt. % of particles having a particle size within the range of about 0.1 to about 10 microns as measured by light scattering in polyether polyol dispersions of the catalyst particles. Preferred paste catalysts of the invention comprise catalyst particles having a bimodal particle size distribution within the range of about 0.1 to about 10 microns.

The invention includes a method for making the paste catalyst. A water-soluble metal salt and a water-soluble metal cyanide salt react in the presence of an organic complexing agent to produce a catalyst slurry. The slurry is washed with aqueous organic complexing agent. Finally, the paste catalyst, which contains DMC compound, complexing agent, and water, is isolated.

The paste catalysts of the invention offer surprising and valuable advantages over powder catalysts typically used in the art. First, catalyst preparation is simpler. Because drying and crushing steps are eliminated, better quality catalysts can be produced in less time and at lower cost compared with powder catalysts. Second, the paste catalysts offer advantages for polyol manufacture. Surprisingly high activity permits rapid polyol preparation at very low catalyst levels. The resulting polyols have narrower molecular weight distributions and lower viscosities compared with polyols made from powder DMC catalysts. Finally, polyols made from the catalysts give low-viscosity, easily processed prepolymers, and give polyurethanes with an excellent balance of physical and mechanical properties.

DETAILED DESCRIPTION OF THE INVENTION

The paste catalysts of the invention comprise a double metal cyanide (DMC) compound, an organic complexing agent, and water. Double metal cyanide compounds useful in the invention are the reaction products of a water-soluble metal salt and a water-soluble metal cyanide salt. The water-soluble metal salt preferably has the general formula $M(X)_n$ in which M is selected from the group consisting of Zn(II), Fe(II), Ni(II), Mn(II), Co(II), Sn(II), Pb(II), Fe(III), Mo(IV), Mo(VI), Al(III), V(V), V(IV), Sr(II), W(IV), W(VI), Cu(II), and Cr(III). More preferably, M is selected from the group consisting of Zn(II), Fe(II), Co(II), and Ni(II). In the formula, X is preferably an anion selected from the group consisting of halide, hydroxide, sulfate, carbonate, cyanide, oxalate, thiocyanate, isocyanate, isothiocyanate, carboxylate, and nitrate. The value of n is from 1 to 3 and satisfies the valency state of M. Examples of suitable metal salts include, but are not limited to, zinc chloride, zinc bromide, zinc acetate, zinc acetonylacetate, zinc benzoate, zinc nitrate, iron(II) sulfate, iron(II) bromide, cobalt(II) chloride, cobalt(II) thiocyanate, nickel(II) formate, nickel (II) nitrate, and the like, and mixtures thereof.

The water-soluble metal cyanide salts used to make the double metal cyanide compounds useful in the invention preferably have the general formula $(Y)_a M'(CN)_b (A)_c$ in which M' is selected from the group consisting of Fe(II), Fe(III), Co(II), Co(III), Cr(II), Cr(III), Mn(II), Mn(III), Ir(III), Ni(II), Rh(III), Ru(II), V(IV), and V(V). More preferably, M' is selected from the group consisting of Co(II), Co(III), Fe(II), Fe(III), Cr(III), Ir(III), and Ni(II). The water-soluble metal cyanide salt can contain one or more of these metals. In the formula, Y is an alkali metal ion or alkaline earth metal ion. A is an anion selected from the group consisting of halide, hydroxide, sulfate, carbonate, cyanide, oxalate, thiocyanate, isocyanate, isothiocyanate, carboxylate, and nitrate. Both a and b are integers greater than or equal to 1; the sum of the charges of a, b, and c balances the charge of M'. Suitable water-soluble metal cyanide salts include, but are not limited to, potassium hexacyanocobaltate(III), potassium hexacyanoferrate(II), potassium hexacyanoferrate(III), calcium hexacyanocobaltate(III), lithium hexacyanoiridate(III), and the like.

Examples of double metal cyanide compounds that can be used in the invention include, for example, zinc hexacyanocobaltate(III), zinc hexacyanoferrate(III), zinc hexacyanoferrate(II), nickel(II) hexacyanoferrate(II), cobalt (II) hexacyanocobaltate(III), and the like. Further examples of suitable double metal cyanide compounds are listed in U.S. Pat. No. 5,158,922, the teachings of which are incorporated herein by reference.

The catalyst compositions of the invention are prepared in the presence of a complexing agent. Generally, the complexing agent must be relatively soluble in water. Suitable complexing agents are those commonly known in the art, as taught, for example, in U.S. Pat. No. 5,158,922. The complexing agent is added either during preparation or immediately following precipitation of the catalyst. As is explained elsewhere in this application, the manner in which the complexing agent is introduced into the DMC complex can be extremely important. Usually, an excess amount of the complexing agent is used. Preferred complexing agents are water-soluble heteroatom-containing organic compounds that can complex with the double metal cyanide compound. Suitable complexing agents include, but are not limited to, alcohols, aldehydes, ketones, ethers, esters, amides, ureas, nitriles, sulfides, and mixtures thereof. Preferred complexing agents are water-soluble aliphatic alcohols selected from the group consisting of ethanol, isopropyl alcohol, n-butyl alcohol, isobutyl alcohol, sec-butyl alcohol, and tert-butyl alcohol. Tert-butyl alcohol is most preferred.

The catalyst also includes water. The amount of water needed is that sufficient to give a paste of desirable consistency. Water and organic complexing agent are typically incorporated into the structure of even powder DMC catalysts; each is present in substantially greater amounts in the paste catalysts of the invention.

The relative amounts of DMC compound, organic complexing agent, and water in the paste catalysts of the invention can vary over a fairly wide range. Preferably, the paste catalyst comprises from about 10 to about 60 wt. % of the DMC compound, from about 40 to about 90 wt. % of the organic complexing agent, and from about 1 to about 20 wt. % of water. More preferred paste catalysts comprise from about 15 to about 40 wt. % of the DMC compound, from about 60 to about 85 wt. % of the organic complexing agent, and from about 5 to about 15 wt. % of water.

Unlike powder DMC catalysts known in the art, the paste DMC catalysts of the invention uniquely comprise at least about 90 wt. % of particles having a particle size within the range of about 0.1 to about 10 microns as measured by light scattering in polyether polyol dispersions of the catalyst particles. Preferably, the paste comprises at least about 90 wt. % of particles having a particle size within the range of about 0.1 to about 5 microns.

Preferred paste catalysts of the invention have a bimodal particle size distribution within the range of about 0.1 to about 10 microns as measured by light scattering in polyether polyol dispersions of the catalyst particles. Preferably, the catalysts contain a major proportion of particles having a particle size within the range of about 1 to about 10 microns, and a minor proportion of particles having a particle size within the range of about 0.1 to about 0.5 microns. The larger particles preferably have a size within the range of about 1 to about 5 microns, and the smaller particles preferably have a size within the range of about 0.15 to about 0.4 microns.

Even the larger particles of the paste catalyst, however, are much smaller in general than typical powder catalyst particles. The large particles in powder catalysts may result from smaller particles aggregating as complexing agent and water are removed during the drying process. Preferred paste catalysts contain few if any particles having particle sizes in excess of about 4 microns. Powder DMC catalysts known in the art have larger particle sizes, typically within the range of about 5 to about 600 microns. In addition, the distribution of powder DMC catalysts is generally unimodal in the 5 to 10 micron range. A major fraction of powder catalyst particles have sizes in excess of 100 microns.

A variety of techniques are suitable for measuring particle size. The particle sizes for catalysts of the invention are conveniently measured by first dispersing the paste catalyst in a polyether polyol (mol. wt. less than about 1000, see Example G), and then measuring the size of the particles in this dispersion by light scattering. One suitable method uses a Leeds & Northrup MICROTRAC X100 particle analyzer, which measures static light scattering properties of the particles. This instrument can be used to approximate the relative amounts of small and larger particles in the paste catalysts.

The very small catalyst particles (i.e., particles having a size less than about 0.5 microns) are often more easily analyzed with quasi-elastic light scattering (QLS). This technique, which measures the dynamic light scattering properties of the particles, is advantageously used to verify the presence and particle size distribution of very small catalyst particles in a sample. Quasi-elastic light scattering is conveniently performed on suspensions of the catalyst particles in a low molecular weight polyol. For example, a suspension of 5 wt. % of DMC catalyst in dipropylene glycol is suitable for use in obtaining QLS measurements. The MICROTRAC method is generally more useful for determining the relative amounts of very small and larger catalyst particles.

In sum, powder DMC catalysts known in the art generally have particle sizes within the range of about 5 to about 600 microns, unimodal distributions within the range of 5 to 10 microns, and no detectable amount of very small particles. In contrast, the paste catalysts of the invention contain at least about 90 wt. % of particles having a particle size within the range of about 0.1 to about 10 microns as measured by light scattering in polyether polyol dispersions of the catalyst particles. Preferred paste catalysts also have a bimodal particle size distribution.

The invention includes methods for making paste catalysts. In general, the paste catalyst can be made from "scratch," or by reconstituting a powder DMC catalyst. The two methods are described further below, and also in Examples A and C.

In one method of the invention, illustrated by Example A, a water-soluble metal salt and a water-soluble metal cyanide salt react in the presence of an organic complexing agent to produce a catalyst slurry. The slurry is washed with an aqueous solution that contains additional organic complexing agent. Finally, a paste catalyst is isolated that contains DMC compound, organic complexing agent and water. The paste comprises at least about 90 wt. % of particles having a particle size within the range of about 0.1 to about 10 microns as measured by light scattering in polyether polyol dispersions of the catalyst particles. Preferably, the paste will contain from about 10 to about 60 wt. % of the DMC compound, from about 40 to about 90 wt. % of the organic complexing agent, and from about 1 to about 20 wt. % of water.

The aqueous solutions of metal salt and metal cyanide salt can be intimately combined (by homogenization, high-shear mixing, or the like) and reacted, as is taught in U.S. Pat. No. 5,470,813, the teachings of which are incorporated herein by reference. The organic complexing agent can be included with either or both of the aqueous salt solutions, or it can be added to the DMC compound immediately following precipitation of the catalyst. It is preferred to pre-mix the organic complexing agent with either the water-soluble metal salt, or with the water-soluble metal cyanide salt, or both, before intimately combining the reactants. Pre-mixing guarantees that the complexing agent will be available during formation of the DMC compound. It enables the preparation of a DMC catalyst having desirable particle size and activity and often eliminates the need for homogenization or high-shear mixing. The pre-mixing technique is described in more detail in application Ser. No. 08/435,116, filed May 15, 1995, now pending.

An important difference in the methods of the invention from the earlier catalyst preparation methods relates to how the paste catalyst is isolated. Prior methods for catalyst preparation teach to dry the catalyst after washing and isolation to give a solid cake. The wet catalyst residues are usually heated in a vacuum oven to remove excess water and organic complexing agent. The dried catalyst is then crushed to give a free-flowing powder. The drying and crushing steps are taught throughout the literature, and are discussed, e.g., in U.S. Pat. No. 3,829,505 and Jap. Pat. Appl. Kokai No. 4-145123.

We surprisingly found that the drying and crushing steps are advantageously eliminated from the catalyst preparation process. The paste catalyst is not just acceptable as an epoxide polymerization catalyst: it even offers substantial advantages over a catalyst that has been dried and crushed to produce the powder form. First, catalyst preparation is simpler. Because two steps—drying and crushing—are eliminated, catalysts are produced in less time and at lower cost. Second, the invention eliminates large capital expenses for drying ovens and pulverizers. Third, higher quality catalysts result because catalyst degradation, which can occur during either the drying or crushing step, is minimized. Fourth, the invention results in catalysts with relatively reproducible particle size distributions; this feature minimizes batch-to-batch variations in catalyst activity, and maximizes batch-to-batch consistency of polyether polyols made from the catalysts. Finally, the invention gives highly active catalysts useful for making high-quality polyether polyols. None of these advantages of paste DMC catalysts is apparent from the prior art, which teaches to dry and crush DMC catalysts and use them in powder form.

A suitable, though less preferred way of making paste catalyst is to make a "reconstituted" paste from a powder DMC catalyst and an organic complexing agent. Water is also optionally added. Any desired method of reconstituting the paste can be used; however, it is important to vigorously combine the powder DMC catalyst with the organic complexing agent to produce a catalyst in which the particles have the desired size and bimodal distribution. In one preferred method, the powder DMC catalyst is combined vigorously with the organic complexing agent and water to produce a reconstituted catalyst slurry. Next, a paste catalyst containing DMC compound, organic complexing agent, and water is isolated. The paste comprises catalyst particles having a bimodal particle size distribution within the range of about 0.1 to about 10 microns as measured by light scattering in polyether polyol dispersions of the catalyst particles. Examples 16 and 17 (Table 4) illustrate the method. As Table 4 shows, DMC paste catalysts made by reconstitution—like paste catalysts made from "scratch"—give excellent results in polyol synthesis.

The invention includes DMC catalyst suspensions made from the paste catalysts. The paste catalyst is simply combined with a starter polyol such as ARCOL PPG-425, PPG-725, or PPG-1025 polyoxypropylene polyols (products of ARCO Chemical Company), or the like, and mixed well to produce a catalyst suspension. This mixture may be stripped to remove volatile materials if desired. The starter polyol preferably has a nominal hydroxyl functionality within the range of 2 to 8, and number average molecular weight within the range of about 200 to about 2000. The suspension preferably has a catalyst solids content within the range of about 1 to about 20 wt. %, more preferably from about 5 to about 15 wt. %. The suspension can then be used as a catalyst for making polyether polyols. Examples 18–20 (Table 5) show how to make a DMC catalyst suspension from a paste catalyst. The polyol preparation method of Example F can be used to make a polyol from a DMC suspension catalyst. As the results in Table 5 show, 8000 mol. wt. diols with low viscosities, narrow molecular weight distributions, and very low unsaturations are consistently made using DMC catalyst suspensions derived from the pastes.

We also surprisingly found that improved DMC catalysts can be prepared by sieving powder DMC catalysts and using only the smallest particles. In particular, improved results are obtained from powder DMC catalysts wherein at least about 90 wt. % of the catalyst particles can pass through a U.S. Standard Sieve of 230 mesh (63 microns). As the results in Table 6 show, an unsieved powder DMC catalyst (Comparative Example 7) initiates polymerization (becomes active) within 7 minutes under the standard reaction conditions (see Example F), and gives an 8000 mol. wt. polyoxypropylene diol having a viscosity of 3480 cks that contains visible particulates of catalyst suspended in the 8000 mol. wt. diol. In contrast, a sample of powder DMC catalyst that passes through 230 mesh (63 microns) initiates faster (within 5 min.), and gives a clear 8000 mol. wt. diol with low viscosity (3260 cks) and narrow molecular weight distribution (Mw/Mn=1.14). Interestingly, the catalyst that passes through 140 mesh and is retained on the 200 mesh screen (Comparative Example 24) is no better than the composite material in terms of initiation time or polyol quality.

The invention includes a process for making an epoxide polymer. The process comprises polymerizing an epoxide in the presence of one of the DMC catalysts of the invention: paste, reconstituted paste, suspension, or sieved powder. Preferred epoxides are ethylene oxide, propylene oxide, butene oxides, styrene oxide, and the like, and mixtures thereof. The process can be used to make random or block copolymers. The epoxide polymer can be, for example, a polyether polyol derived from the polymerization of an epoxide in the presence of a hydroxyl group-containing initiator.

Other monomers that will copolymerize with an epoxide in the presence of a DMC compound can be included in the process of the invention to make other types of epoxide polymers. Any of the copolymers known in the art made using conventional DMC catalysts can be made with the catalysts of the invention. For example, epoxides copolymerize with oxetanes (as taught in U.S. Pat. Nos. 3,278,457 and 3,404,109) to give polyethers, or with anhydrides (as taught in U.S. Pat. Nos. 5,145,883 and 3,538,043) to give polyester or polyetherester polyols. The preparation of polyether, polyester, and polyetherester polyols using double metal cyanide catalysts is fully described, for example, in U.S. Pat. Nos. 5,223,583, 5,145,883, 4,472,560, 3,941,849, 3,900,518, 3,538,043, 3,278,458, and in J. L. Schuchardt and S. D. Harper, *SPI Proceedings, 32nd Annual Polyurethane Tech./Market. Conf.* (1989) 360. The teachings of all of these U.S. patents related to polyol synthesis using DMC catalysts are incorporated herein by reference.

The paste catalysts of the invention are highly active, and like the catalysts taught in U.S. Pat. No. 5,470,813, are active enough to be used at extremely low catalyst levels. At catalyst levels of 50 or 25 ppm or less, the catalyst can often be left in the polyol, thereby eliminating the need for a back-end purification step. As Table 2 shows, paste DMC catalysts offer distinct advantages compared with even the best powder catalysts. At the same catalyst level, the paste initiates faster, and gives a polyol with better properties, including lower viscosity, narrower molecular weight distribution, and higher clarity. As Table 3 shows, the paste DMC catalysts of the invention give polyols with low viscosity and narrow molecular weight distribution even when the propylene oxide (PO) feed time is substantially reduced. Compare the polyols of Example 11 (paste catalyst, 6 h feed time for PO) with those of Comparative Example 12. These results demonstrate the advantages of paste DMC catalysts over the best known powder DMC catalysts.

Polyols made from the catalysts of the invention have low viscosities. In turn, polyurethane prepolymers made from these polyols also have relatively low viscosities, which makes them more easily processed. Polyurethane foams, sealants, elastomers, and coatings made from the polyols and prepolymers have an excellent balance of physical and mechanical properties that result from the low unsaturation, low viscosity, and narrow molecular weight distribution of these polyols.

The following examples merely illustrate the invention; those skilled in the art will recognize many variations that are within the spirit of the invention and scope of the claims.

EXAMPLE A

Preparation of a Paste Zinc Hexacyanocobaltate Catalyst

A one-liter round-bottom flask equipped with mechanical stirrer, addition funnel, and thermometer is charged with distilled water (604 g), potassium hexacyanocobaltate (14.8 g), and tert-butyl alcohol (78 g). The mixture is stirred until all of the cobalt salt dissolves. The resulting solution is heated to 30° C. A solution of zinc chloride in water (50 wt. % zinc chloride, 304 g of solution) is added over 50 min. with stirring. Stirring continues for another 30 min. at 30° C. The resulting white suspension is centrifuged. A wet cake of solids is isolated, and is resuspended with vigorous stirring in a solution of tert-butyl alcohol (204 g) and water (112 g). After all of the solids are completely suspended in the wash solution, the mixture is stirred for 30 min. The suspension is again centrifuged, and the wet solids are isolated. The solids are resuspended in 99.5% tert-butyl alcohol (288 g), centrifuged, and isolated as described above. The resulting paste contains about 24 wt. % zinc hexacyanocobaltate complex, the remainder being tert-butyl alcohol (about 64 wt. %), and water (about 12 wt. %). A sample of this paste catalyst is used "as is" as a catalyst for polyol synthesis. See Tables 1–5.

COMPARATIVE EXAMPLE B

Preparation of a Powder Zinc Hexacyanocobaltate Catalyst

A sample of the paste catalyst prepared in Example A is converted to a dry powder as follows. The paste catalyst sample is dried to a constant weight in a vacuum oven at 45° C. The resulting hard, brittle dry mass is pulverized using a mortar and pestle to produce a free-flowing powder. A sample of this powder catalyst is used for polyol synthesis. See Tables 1–3 and 6.

EXAMPLE C

Preparation of a Reconstituted Paste DMC Catalyst from Powder

A sample of the catalyst of Comparative Example B (powder catalyst) is converted to a reconstituted paste catalyst as follows. A suspension of powder catalyst (33 wt. %) in t-butyl alcohol is prepared by combining and homogenizing the components. Water (10 wt. %) is added, and the mixture is homogenized to achieve rapid, vigorous mixing. The suspension thickens to a paste. The paste is used "as is" as a catalyst for polyol synthesis. See Table 4.

EXAMPLE D

Preparation of a DMC Catalyst Suspension from a Paste Catalyst

A sample of the catalyst of Example A is combined with ARCOL PPG-425 (product of ARCO Chemical Company, a 425 mol. wt. polyoxypropylene diol), and the mixture is homogenized at low speed to produce a catalyst suspension of uniform distribution that contains about 10 wt. % solids. This mixture is fluid, and solids settle from it easily. The suspension is stripped under vacuum (20–30 mm Hg) to remove volatile materials at low temperature (40°–45° C.; low enough to prevent catalyst deactivation). The resulting catalyst suspension contains 13.7 wt. % solids. The suspension is fluid; slight settling of solids with time is apparent.

The catalyst suspension is used "as is" as a catalyst for polyol synthesis.

A similar suspension catalyst is prepared using ARCOL PPG-725 (760 mol. wt. polyoxypropylene diol) or PPG-1025 (1000 mol. wt. polyoxypropylene diol), both products of ARCO Chemical Company. The stripped suspension from the PPG-725 diol is a liquid, while the one from the PPG-1025 diol is more like a paste. Each of these suspensions is used "as is" as a catalyst for polyol synthesis. See Table 5.

EXAMPLE E

Preparation of a Sieved DMC Catalyst

Chunks of a powder zinc hexacyanocobaltate catalyst, prepared as in Comparative Example B, are pulverized as described in that example, and are placed on the top tray of a stack of U.S. Standard Sieve Series trays (meeting ASTM E-11 specifications). The sieve trays and accessories are stacked in the following order (from top to bottom): cover, 50 mesh, 100 mesh, 140 mesh, 200 mesh, 230 mesh, 325 mesh, 400 mesh, and bottom pan. The stack is placed on a Model RX-24 Sieve Shaker (product of Tyler Industries) and the stack is shaken for 30 min. The samples left on each screen are used as catalysts for polyol synthesis. See Table 6.

EXAMPLE F

Preparation of Polyoxypropylene Diols (8K Mol. Wt.): General Procedure

A two-gallon reactor is charged with ARCOL PPG-725 polyoxypropylene diol (760 mol. wt., 618 g) and zinc hexacyanocobaltate/tert-butyl alcohol complex catalyst (paste, powder, reconstituted paste, or slurry; amounts shown in Tables 2–6). The reactor is purged several times with dry nitrogen. The mixture is stirred, and a vacuum (2 psia) is applied to the reactor. The stirred mixture is heated to 130° C. Propylene oxide (72 g) is added. Additional propylene oxide is not added until an accelerated pressure drop occurs in the reactor, which indicates activation of the catalyst. After the catalyst activation is apparent, the remaining propylene oxide (5810 g) is added to the reactor over 12 h at a constant rate of about 8 g/min. After propylene oxide addition is complete, the mixture is held at 130° C. for 1 h. Residual unreacted propylene oxide is stripped from the polyol product under vacuum. The polyol is then cooled to 80° C. and discharged from the reactor. The resulting polyoxypropylene diol of about 8000 mol. wt. is characterized (see Tables 2–6 for properties).

EXAMPLE G

Preparation of Samples for MICROTRAC X-100 Particle Size Analysis

A suspension of 250 ppm of zinc hexacyanocobaltate catalyst in a 725 mol. wt. polyoxypropylene diol (PPG-725 diol) is prepared as follows. The catalyst sample (paste or powder, 0.15 g on a dry catalyst basis) is placed on the surface of 25 g of PPG-725 diol in a beaker. (When a paste catalyst is used, the amount of paste required is 0.15 g divided by the weight percent of DMC catalyst in the paste.) Additional PPG-725 diol (125 g) is added to the beaker. The contents are mixed well using a mechanical stirrer until the solids are uniformly dispersed in the polyol. This catalyst suspension is then added with stirring to an additional 450 g of PPG-725 diol. Stirring continues until a uniform suspension results.

The preceding examples are meant only as illustrations. The following claims define the scope of the invention.

TABLE 1

Particle Size Analysis[3] of Double Metal Cyanide Catalysts

| Ex. # | Catalyst form | Particle size distribution (0.1–10 μm range) | Particle size (μm) |
|---|---|---|---|
| 1 | Paste[1] | Bimodal | 0.1–0.2 (minor component) 0.9–4.0 (major component) |
| C2 | Powder[2] | Unimodal | 4.6–600 |

[1]Paste catalyst = zinc hexacyanocobaltate/tert-butyl alcohol complex prepared as in Example A.
[2]Powder catalyst = zinc hexacyanocobaltate/tert-butyl alcohol complex prepared as in Comp. Example B.
[3]Example G describes sample preparation. Suspensions of 250 ppm of DMC catalyst in PPG-725 diol are analyzed by light scattering using a Leeds & Northrup MICROTRAC X100 particle size analyzer. Suspensions of 5 wt. % of DMC catalyst in dipropylene glycol are also analyzed by quasi-elastic light scattering (QLS). The QLS analysis confirms the presence of very small (0.1–0.2 μm) particles in the paste catalyst of Example 1.

TABLE 2

Paste v. Powder DMC Catalysts: Effect of Catalyst Concentration on Initiation and Polyol Properties

| Ex. # | Catalyst form | Catalyst level (ppm) | Initiation time (min) | Polyol properties[3] | | |
|---|---|---|---|---|---|---|
| | | | | Mw/Mn | Viscosity (cks) | Appearance |
| 3 | Paste[1] | 50 | <<1 | 1.06 | 2910 | Clear |
| 4 | Paste | 25 | <1 | 1.07 | 2940 | Clear |
| 5 | Paste | 13 | 2.0 | 1.15 | 3190 | Clear |
| 6 | Paste | 9.4 | 2.5 | 1.21 | 3470 | Clear |
| C7 | Powder[2] | 25 | 7.0 | 1.21 | 3480 | Particulates |
| C8 | Powder | 13 | 15 | >>1.6 | 5790 | Particulates |

[1]Paste catalyst = zinc hexacyanocobaltate/tert-butyl alcohol complex prepared as in Example A.
[2]Powder catalyst = zinc hexacyanocobaltate/tert-butyl alcohol complex prepared as in Comp. Example B.
[3]Polyol = 8K mol. wt. polyoxypropylene diol prepared as in Example F.

TABLE 3

Effect of Epoxide Feed Time on Polyol Properties

| Ex. # | Catalyst form | PO feed time (h) | Polyol properties[3] | |
|---|---|---|---|---|
| | | | Viscosity (cks) | Mw/Mn |
| 9 | Paste[1] | 12 | 3110 | 1.08 |
| 10 | Paste | 8 | 3010 | 1.08 |
| 11 | Paste | 6 | 3050 | 1.11 |
| C12 | Powder[2] | 12 | 3480 | 1.20 |
| C13 | Powder | 8 | 4860 | 1.43 |

[1]Paste catalyst = zinc hexacyanocobaltate/tert-butyl alcohol complex prepared as in Example A.
[2]Powder catalyst = zinc hexacyanocobaltate/tert-butyl alcohol complex prepared as in Comp. Example B.
[3]Polyol = 8K mol. wt. polyoxypropylene diol prepared as in Example F.

TABLE 4

Polyols from DMC Paste vs. Reconstituted DMC Catalysts

| Ex. # | Catalyst form | Initiation time (min) | Polyol properties[3] Viscosity (cks) | Mw/Mn |
|---|---|---|---|---|
| 14 | Paste[1] | <1 | 2910 | 1.07 |
| 15 | Paste | <1 | 2890 | 1.06 |
| 16[4] | Reconstituted paste[2] | <1 | 3060 | 1.08 |
| 17[4] | Reconstituted paste | <1 | 3020 | 1.09 |

[1]Paste catalyst = zinc hexacyanocobaltate/tert-butyl alcohol complex prepared as in Example A.
[2]Reconstituted paste catalyst = zinc hexacyanocobaltate/tert-butyl alcohol complex prepared as in Ex. C.
[3]8K mol. wt. polyoxypropylene diols are made as in Example F using 25 ppm catalyst and 12 hour feed time for propylene oxide.
[4]The PPG-725/PO ratio for these runs is decreased to reach the target hydroxyl number of 14 mg KOH/g.

TABLE 5

Polyols from Suspensions of DMC Paste Catalyst in Starter Polyols

| Ex. # | Catalyst | Starter diol for suspension | OH # (mg KOH/g) | Viscosity (cks) | Mw/Mn | Unsaturation (meq/g) |
|---|---|---|---|---|---|---|
| 10 | Paste[1] | none | 14.3 | 3010 | 1.08 | 0.0042 |
| 18 | Suspension[2] | PPG-425 | 13.8 | 3230 | 1.12 | 0.0048 |
| 19 | Suspension | PPG-725 | 14.1 | 3190 | 1.11 | 0.0047 |
| 20 | Suspension | PPG-1025 | 14.1 | 3150 | 1.11 | 0.0047 |

[1]Paste catalyst = zinc hexacyanocobaltate/tert-butyl alcohol complex prepared as in Example A.
[2]Suspension catalyst = mixture of starter diol (ARCOL PPG-425, -725, or -1025) and paste catalyst (13.7 wt. % solids).
[3]8K mol. wt. polyoxypropylene diols are made as in Example F using 25 ppm catalyst and 8 hour feed time for propylene oxide.

TABLE 6

Effect of Sieving Powder DMC Catalyst on Catalyst Performance

| Ex. # | Sieve mesh Passes through | Sieve mesh Retained on | Sieve opening (μm) Passes through | Sieve opening (μm) Retained on | Initiation time (min) | Polyol properties[2] Viscosity | Mw/Mn | Appearance |
|---|---|---|---|---|---|---|---|---|
| C7 | composite[1] | | ---- | | 7.0 | 3480 | 1.21 | particulates |
| C22 | ---- | 50 | ---- | 297 | 12 | 7280 | <<1.6 | particulates |
| C23 | 50 | 100 | 297 | 149 | 10 | 3860 | 1.27 | particulates |
| C24 | 140 | 200 | 104 | 74 | 8.0 | 3490 | 1.20 | particulates |
| 25 | 230 | 325 | 63 | 44 | 5.0 | 3260 | 1.14 | clear |

[1]Powder catalyst of Comparative Example B; not sieved.
[2]Polyol = 8K mol. wt. polyoxypropylene diol prepared as in Example F.

We claim:

1. A process for making an epoxide polymer, said process comprising polymerizing an epoxide in the presence of a catalyst which comprises from about 10 to about 60 wt. % of a double metal cyanide (DMC) compound, from about 40 to about 90 wt. % of an organic complexing agent, and from about 1 to about 20 wt. % of water, wherein the catalyst comprises at least about 90 wt. % of particles having a particle size within the range of about 0.1 to about 10 microns as measured by light scattering in polyether polyol dispersions of the catalyst particles.

2. The process of claim 1 wherein the double metal cyanide compound is a zinc hexacyanocobaltate.

3. The process of claim 1 wherein the organic complexing agent is tert-butyl alcohol.

4. The process of claim 1 wherein the epoxide is selected from the group consisting of ethylene oxide, propylene oxide, butene oxides, styrene oxides, and mixtures thereof.

5. The process of claim 1 wherein the catalyst particles have a bimodal particle size distribution within the range of about 0.1 to about 10 microns.

6. A process for making an epoxide polymer, said process comprising polymerizing an epoxide in the presence of a catalyst which comprises from about 10 to about 60 wt. % of a double metal cyanide (DMC) compound, from about 40 to about 90 wt. % of an organic complexing agent, and from about 1 to about 20 wt. % of water, wherein the catalyst comprises catalyst particles having a bimodal particle size distribution within the range of about 0.1 to about 10 microns as measured by light scattering in polyether polyol dispersions of the catalyst particles.

7. The process of claim 6 wherein the double metal cyanide compound is a zinc hexacyanocobaltate.

8. The process of claim 6 wherein the organic complexing agent is tert-butyl alcohol.

9. The process of claim 6 wherein the epoxide is selected from the group consisting of ethylene oxide, propylene oxide, butene oxides, styrene oxides, and mixtures thereof.

10. A process for making an epoxide polymer, said process comprising polymerizing an epoxide in the presence of a catalyst which comprises from about 15 to about 40 wt. % of zinc hexacyanocobaltate, from about 60 to about 80 wt. % of tert-butyl alcohol, and from about 5 to about 15 wt. % of water, wherein the catalyst comprises at least about 90 wt. % of particles having a particle size within the range of about 0.1 to about 10 microns as measured by light scattering in polyether polyol dispersions of the catalyst particles.

11. The process of claim 10 wherein the epoxide is selected from the group consisting of ethylene oxide, propylene oxide, butene oxides, styrene oxides, and mixtures thereof.

* * * * *